United States Patent [19]

Gallick-Whitaker

[11] Patent Number: 4,537,965

[45] Date of Patent: Aug. 27, 1985

[54] METHOD OF PREPARING 4AR,8AR-5-PERMISSIBLY SUBSTITUTED-6-OXO-OCTAHYDRO-1H(AND 2H)-PYRAZOLO[3,4-G]QUINOLINES, USEFUL AS INTERMEDIATES

[75] Inventor: Nancy G. Gallick-Whitaker, Indianapolis, Ind.

[73] Assignee: Eli Lilly and Company, Indianapolis, Ind.

[21] Appl. No.: 637,354

[22] Filed: Aug. 3, 1984

[51] Int. Cl.$^3$ ............................................. C07D 471/12
[52] U.S. Cl. ......................................... 546/82; 546/84
[58] Field of Search ..................... 546/82, 84; 424/258

[56] References Cited

U.S. PATENT DOCUMENTS 4,198,415  4/1980  Kornfeld et al. ................... 424/258

OTHER PUBLICATIONS

Hahn et al., *J.P.E.T.*, 224, 206 (1982).

*Primary Examiner*—Henry R. Jiles
*Assistant Examiner*—P. Ann Bucci
*Attorney, Agent, or Firm*—James L. Rowe; Arthur R. Whale

[57] ABSTRACT

4aR,8aR-5-permissibly substituted-6-oxo-octahydro-1H(and 2H)-pyrazolo[3,4-g]quinolines. The compounds are useful as intermediates in preparing dopamine D-2 agonists.

3 Claims, No Drawings

METHOD OF PREPARING 4AR,8AR-5-PERMISSIBLY SUBSTITUTED-6-OXO-OCTAHYDRO-1H(AND 2H)-PYRAZOLO[3,4-G]QUINOLINES, USEFUL AS INTERMEDIATES

BACKGROUND OF THE INVENTION

Kornfeld and Bach, U.S. Pat. No. 4,198,415 claim trans-(±)-5-permissibly substituted-4,4a,5,6,7,8,8a,9-octahydro-1H-pyrazolo[3,4-g]quinolines and their tautomers, the corresponding 2H derivative (I and II below) useful as dopamine D-2 agonists.

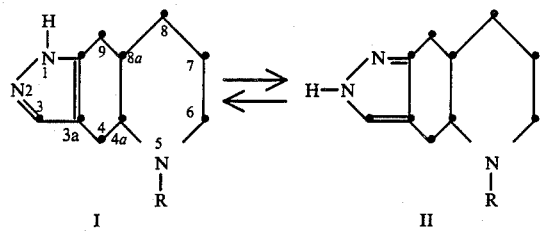

wherein R is $C_{1-3}$ straight-chain alkyl (methyl, ethyl, n-propyl) or allyl.

Each tautomer consists of two enantiomers, the 4aR,-8aR and 4aS,8aS derivatives. These four enantiomers are pictured below—Ia and Ib for the 1H tautomers; IIa and IIb for the 2H tautomers.

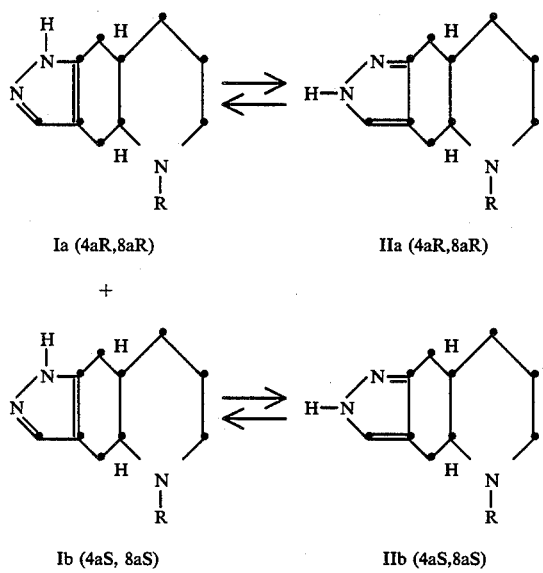

The copending application of Titus and Kornfeld Ser. No. 439,238 filed 11/3/82 discloses a method of separating the tautomer pair I and II into their respective enantiomers (Ia and Ib or IIa or IIb) where R is n-propyl. Alternatively, the same enantiomers are prepared by using an optically-active intermediate. The copending application of Schaus and Booher, Ser. No. 639,107, also filed 11/3/82, separates the trans-(±)-1-alkyl(-specifically n-propyl)-6-oxodecahydroquinoline into its enantiomers, 4aR,8aR-1-n-propyl-6-oxodecahydroquinoline (III) and its 4aS,8aS-1-n-propyl-6-oxodecahydroquinoline (IV).

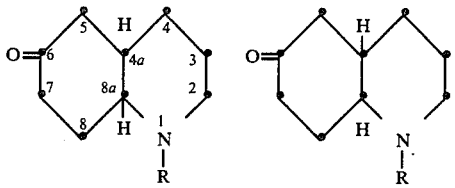

Reaction of III with the dimethyl acetal of dimethylformamide or tris dimethylaminomethane forms a 7-dimethylaminomethylene derivative, reaction of which with $NH_2NH_2$ yields the tautomeric enantiomer, Ia⇌IIa.

The tautomeric pair Ia⇌IIa has been found to be useful in treating both hypertension and sexual dysfunction in mammals, see Hahn et al, *J.P.E.T.*, 224, 206 (1982) and the copending application of Foreman, Ser. No. 518,906 filed 8/1/83.

The metabolism of the enantiomeric tautomers, Ia⇌IIa, in mammals has not hitherto been disclosed nor have ring-oxygenated derivatives of trans-(±)-5-permissibly-substituted-4,4a,5,6,7,8,8a,9-octahydro-1H(and 2H)-pyrazolo[3,4-g]quinolines.

SUMMARY OF THE INVENTION

This invention provides 4aR,8aR-5-permissibly-substituted-6-oxo-4,4a,5,6,7,8,8a,9-octahydro-1H-pyrazolo[3,4-g]quinolines, formula Xa, the 2H tautomers, formula Xb, and pharmaceutically acceptable acid addition salts thereof

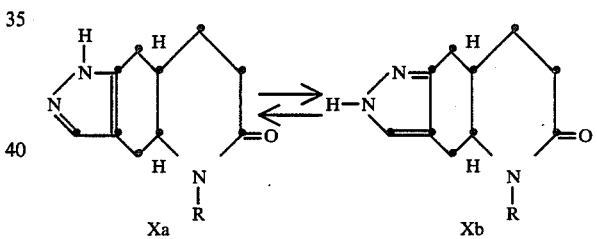

wherein R is methyl, ethyl, n-propyl, allyl or H.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The tautomeric pair Xa⇌Xb when R is n-propyl is prepared by feeding a tautomeric pair according to Ia⇌IIa to a mammal—rat, mouse, dog or monkey—and isolating the corresponding 6-oxo derivative from urine collected during said feeding period. HPLC is employed to effect the separation of the desired metabolite from other co-produced metabolites. The 6-oxo derivative where R=H is also isolated. Other tautomeric pairs according to Ia⇌IIa when R is methyl, ethyl or allyl are metabolized in similar fushion, through the absolute quantities of each metabolite may vary.

SPECIFIC EMBODIMENT OF THE INVENTION

A typical preparation of a compound according to Xa⇌XIa wherein R is H or N-propyl follows:

Rhesus monkeys were given a 2 mg/kg or 20 mg/kg nasogastric dose of Xa where R is n-propyl, radiolabeled at C-3. Urine from monkeys given a 2 mg/kg (or 20 mg/kg) nasogastric dose of $^{14}$C-4aR,8aR-5-n-propyl-4,4a,5,6,7,8,8a,9-octahydro-1H(and 2H)-pyrazolo[3,4-g]quinoline was applied to a Dianion HP-20 column. The column was washed with water until radioactivity was detected in the eluate. The radioactivity (ave. 94%) was then eluted with methanol. Radioactivity in the residue that resulted upon evaporation of the methanolic fraction was then selectively dissolved in a minimal volume of various organic solvents (methanol, ethanol, and ethanol, ethyl acetate (2:1)). This treatment caused precipitation of endogenous substances and allowed the radioactivity to be concentrated in a small volume of methanol suitable for thin-layer chromatography on silica gel plates [chloroform/methanol/15N ammonium hydroxide (50:45:5)]. Autoradiography of the developed TLC plates revealed five broad bands. Regions corresponding to the bands were scraped from the plates, the radioactive metabolites eluted from the scrapings with methanol, and the eluates evaporated to dryness under reduced pressure.

The radioactive material eluted from the TLC band ($R_f$=0.58–0.85) was dissolved in deionized water and the pH adjusted to ca. 12 with 0.01N aqueous NaOH. The desired radioactive metabolites were extracted into ethyl acetate. Evaporation of the combined ethyl acetate extracts yielded a residue which was dissolved in 0.001N HCl.

The acidic aqueous layer was extracted with ethyl acetate, and the ethyl acetate extracts discarded. The pH of the aqueous layer was then adjusted to ca. 12 with 5N NaOH and the radioactive metabolite was extracted into ethyl acetate. The ethyl acetate extracts were evaporated to dryness under reduced pressure, and the resulting residue was dissolved in deionized water. Injection of this aqueous layer into the following HPLC solvent system: 100% water-5 min; 0–100% methanol-37.5 min at 2 ml/min flow rate (using an Alltech, C8, 10μ column). This procedure gave the tautomeric pair, 4aR,8aR-6-oxo-4,4-a,5,6,7,8,8a,9-octahydro-1H(and 2H)-pyrazolo[3,4-g]quinoline, in substantially pure form. The product was further purified by HPLC using the same solvent system with a Whatman Partisil 5, OD-3, RAC column.

The compound thus purified had the following physical characteristics:

Mass spectrum (Field desorption); molecular ion at 191; (High resolution electron impact) 191 (molecular ion), 119. 94.

Infrared spectrum: (CHCl$_3$) 1660 cm$^{-1}$ (lactam carbonyl).

NMR (CDCl$_3$()) δ at 7.34 (H3), ~2.5 (H4ax), 2.89 (H4eq), 3.41 (H4a), ~2.5 (H7ax), ~2.6 (H7eq), 1.70 (H8ax), 2.05 (H8eq), 1.90 (H8a), ~2.4 (H9ax), 2.99 (H9eq).

Using the same TLC fraction as above ($R_f$=0.58–0.85), the radioactive material was dissolved in 0.01 N aqueous NaOH and the radioactive material was extracted into ethyl acetate. The ethyl acetate extract was washed with 0.001N HCl. The pH of the acidic aqueous layer was adjusted to neutrality using 1N aqueous NaOH. Injection of the aqueous extract onto the following HPLC system: 100% water 5 min; 0–100% methanol 37.5 min at a 2 ml/min flow rate (Whatman Partisil 5, ODS-3, RAC column). This procedure gave the tautomeric pair 4aR,8aR-5-n-propyl-6-oxo-4,4a,5,6,7,8,8a,9-octahydro-1H(and 2H)-pyrazolo[3,4-g]quinoline. The product was further purified by HPLC using with the following solvent system but the same column:100% water-7 min; 0–60% methanol-20 min at a 2 ml/min flow rate. The compound thus purified had the following physical characteristics:

Mass Spectrum (Field desorption); molecular ion at 233; (High resolution electron impact) 233 (molecular ion), 204,190,176,119,94.

Infrared spectrum (CHCl$_3$): 1626 cm$^{-1}$ (lactam carbonyl).

NMR (CDCl$_3$): δ at 7.37 (H3), 3.21 (H4eq), 2.39 (H4ax), 3.34 (H4a), 2.56 (7eq), 2.48 (H7ax), 1.94 (H8eq), 1.63 (H8ax), 1.94 (H8a), 2.97 (H9eq), 2.48 (H9ax), 3.75 and 3.23 (H10), 1.71 and 1.50 (H11), 0.92 (H12).

The compounds of this invention are useful intermediates in that they can be converted by LiAlH$_4$ or the like reducing agent to the corresponding pyrazolo[3,4-g]quinoline; ie., treatment of 4aR,8aR-5-n-propyl-6-oxo-4,4a,5,6,7,8,8a,9-octahydro-1H(and 2H)-pyrazolo[3,4-g]quinoline yields the dopamine D-2 agonist, quinpirole (4aR,8aR-5-n-propyl-4,4a,5,6,7,8,8a,9-octahydro-1H(and 2H)-pyrazolo[3,4-g]quinoline).

4aR,8aR-6-oxo-4,4a,5,6,7,8,8a,9-octahydro-1H(and 2H)-pyrazolo[3,4-g]quinoline can be reduced with LiAlH$_4$ to 4aR,8aR-4,4a,5,6,7,8,8a,9-octahydro-1H(and 2H)-pyrazolo[3,4-g]quinoline and that compound alkylated or allylated with an alkyl or allyl halide and base to yield the 4aR,8aR dopamine D-2 agonists, or it can be alkylated or allylated as with methyl, ethyl or n-propyl iodide or allyl chloride in the presence of a base to the corresponding 5-methyl, ethyl or n-propyl derivative, and that compound reduced with LiAlH$_4$ to the desired 4aR,8aR-5-alkyl or allyl-octahydropyrazolo[3,4-g]quinoline tautomeric pair, active dopamine D-2 agonists.

Racemic trans-(±)-5-n-propyl-4,4a,5,6,7,8,8a,9-octahydro-1H(and 2H)-pyrazolo[3,4-g]quinoline is also metabolized by mammals to the above 4aR,8aR-6-oxo derivative. Similarly, mammals will metabolize 4aR,-8aR-5-methyl or ethyl or allyl-4,4a,5,6,7,8,8a,9-octahydro-1H(and 2H)-pyrazolo[3,4-g]quinoline to both the des-N-alkyl lactam and the N-methyl or ethyl or allyl lactam as shown above with the N-n-propyl derivatives.

The copending application of Schaus, Ser. No. 637,665, filed this even date, describes procedures for obtaining trans-(±)-5-C$_{1-3}$ straight-chain alkyl or allyl-6-oxo-4,4a,5,6,7,8,8a,9-octahydro-1H(and 2H)- pyrazolo[3,4-g]quinolines as well as the individual enantiomers the 4aR,8aR and 4aS,8aS stereoimomers.

The compounds represented by this invention have one weakly basic amine groups, the pyrazole-ring nitrogen carrying the hydrogen. Salts can be formed with this basic group by using one equivalent of a strong acid per equivalent of base. The stronger organic and inorganic acids which will form salts with the bases of this invention, include the mineral acids, toluenesulfonic acid, methanesulfonic acid etc. Hydrochloride salts are conveniently prepared by dissolving the free base in ether, saturating the ethereal solution with gaseous HCl, and recovering the hydrochloride salt by filtration. Other salts can be prepared by mixing a solution of the base with a solution containing one equivalent of the strong acid, and recovering the salt by evaporation of the solvent.

I claim:

1. A tautomeric pair of the formula

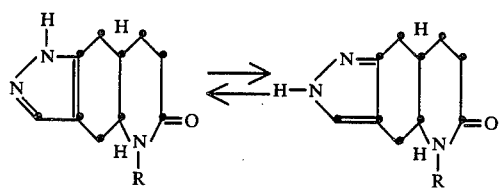

wherein R is H, $C_{1-3}$ straight-chain alkyl or allyl, and pharmaceutically acceptable acid addition salts thereof.

2. A tautomeric pair according to claim 1, said pair being 4aR,8aR-5-n-propyl-6-oxo-4,4a,5,6,7,8,8a,9-octahydro-1H(and 2H)-pyrazolo[3,4-g]quinoline.

3. A tautomeric pair according to claim 1, said pair being 4aR,8aR-6-oxo-4,4a,5,6,7,8,8a,9-octahydro-1H(and 2H)-pyrazolo[3,4-g]quinoline.

* * * * *